United States Patent
Young et al.

Patent Number: 5,823,960
Date of Patent: Oct. 20, 1998

[54] IMAGING SYSTEMS

[75] Inventors: Ian Robert Young, Nr. Marlborough, England; James Michael McNally, Geauga County, Ohio

[73] Assignee: Picker International, Inc., Cleveland, Ohio

[21] Appl. No.: 688,038

[22] Filed: Jul. 26, 1996

[30] Foreign Application Priority Data

Jul. 27, 1995 [GB] United Kingdom .................. 9515446

[51] Int. Cl.⁶ .................................................. G61B 5/055
[52] U.S. Cl. ........................................... 600/415; 600/417
[58] Field of Search .............................. 128/653.1, 653.2, 128/660.01; 606/130; 378/62–65; 600/407, 410, 437, 411, 415, 417

[56] References Cited

U.S. PATENT DOCUMENTS

| | | |
|---|---|---|
| 4,242,587 | 12/1980 | Lescrenier . |
| 5,042,485 | 8/1991 | Pfeiler et al. . |
| 5,748,700 | 5/1998 | Shepherd et al. .......................... 378/65 |

FOREIGN PATENT DOCUMENTS

| | | |
|---|---|---|
| 0151910 | 8/1985 | European Pat. Off. . |
| 0419729 | 4/1991 | European Pat. Off. . |
| 0531081 | 3/1993 | European Pat. Off. . |
| 0558029 | 9/1993 | European Pat. Off. . |
| 0562585 | 9/1993 | European Pat. Off. . |
| 0600610 | 6/1994 | European Pat. Off. . |
| WO 9502995 | 2/1995 | WIPO . |

*Primary Examiner*—Brian Casler
*Attorney, Agent, or Firm*—T. B. Gurin; J. J. Fry

[57] ABSTRACT

An imaging system produces an image of an internal part of an object and a representation of a tool, which representation corresponds to the position of the tool with respect to the actual object. An imaging apparatus defines an examination region. After an image of the object is obtained, the object is moved to a treatment position fixed in relation to the examination region. The object is supported on a moveable table, which is in turn supported on a pair of rails. A reference frame mounted to the imaging apparatus carries radiation detectors for detecting radiation emitted by emitters on a surgical tool. The position of the tool with respect to the reference frame, and hence with respect to the actual object, can therefore be determined.

28 Claims, 2 Drawing Sheets

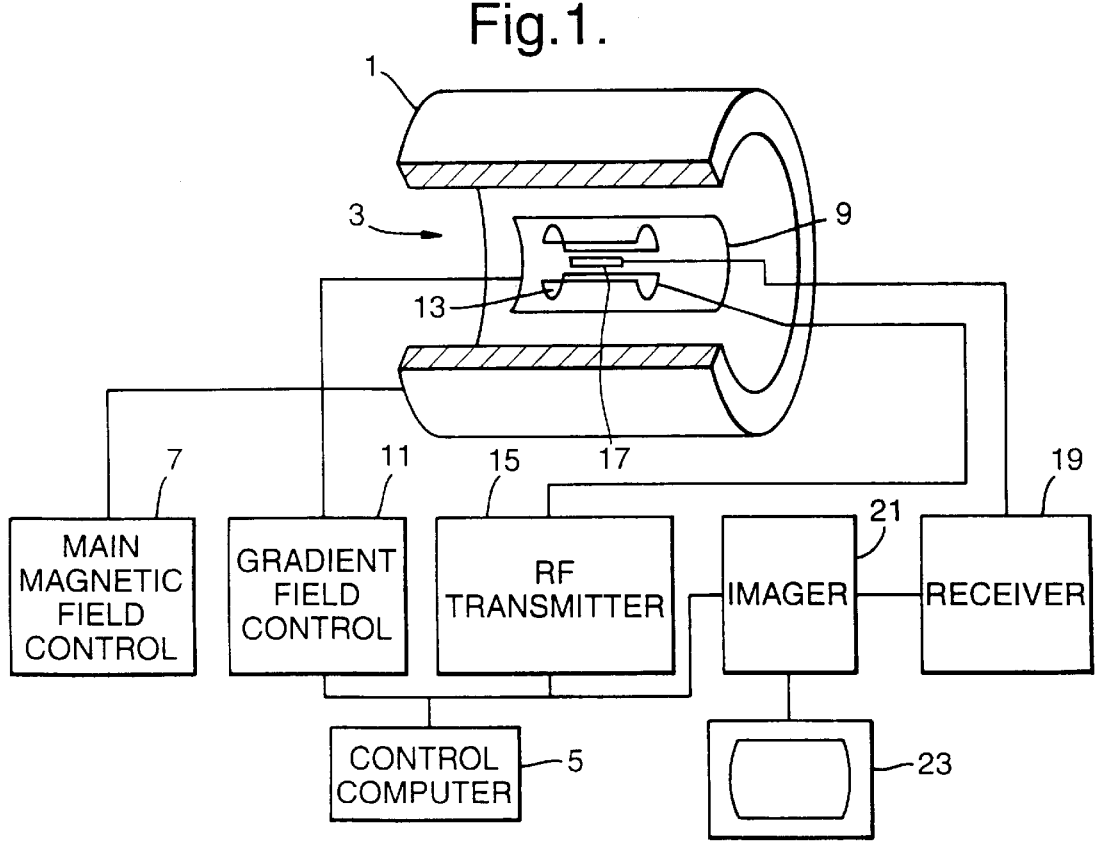

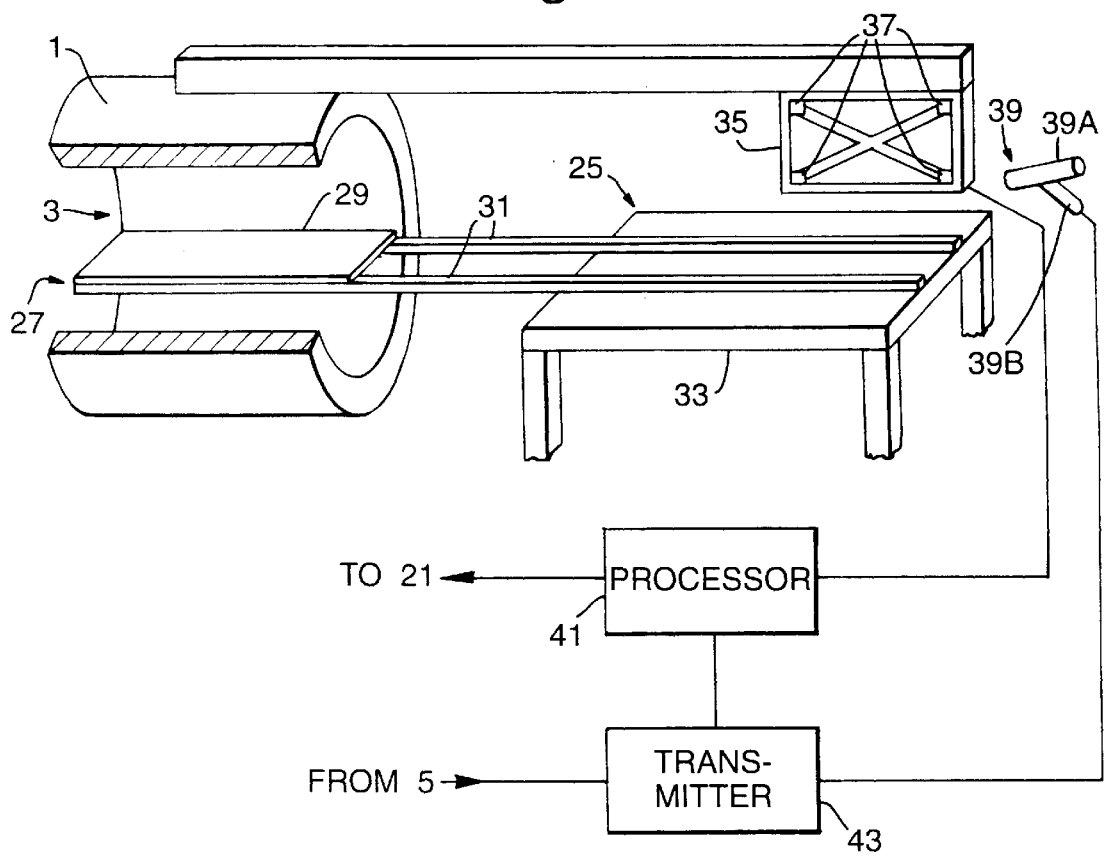
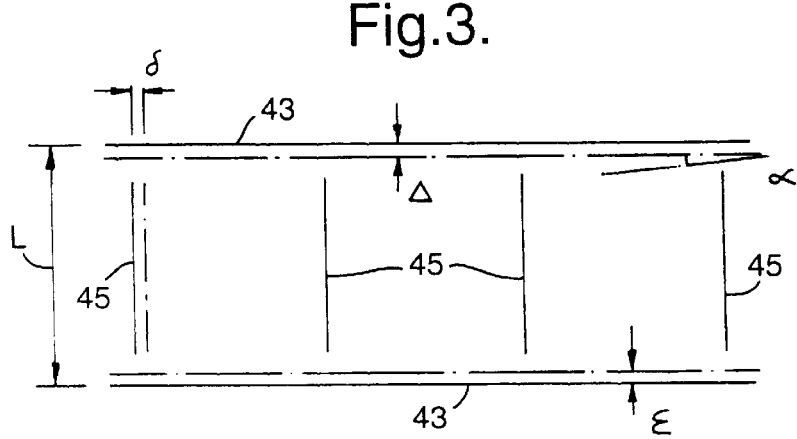

IMAGING SYSTEMS

This invention relates to imaging systems.

More particularly the invention relates to imaging systems of the kind capable of producing a display comprising an image of an internal part of an object and a representation of a tool at a position in the display with respect to the image of the object corresponding to the position of the tool with respect to the actual object.

Such an imaging system finds application, for example, in medical stereotactic surgical procedures. By using the system a surgeon may position a surgical tool, such as a scalpel or drill, with respect to a patient's body so as to make an incision at the most appropriate position to gain access to selected interior parts of the patient's body.

Known forms of such a system comprise an imaging apparatus, such as an x-ray computed tomography (CT) apparatus, for displaying an image of an internal part, e.g. a sectional view through the body of a patient to be treated. The system further includes a set of markers which are attached to the body of the patient to be treated and appear in the displayed image.

The system further includes a rigid reference frame which carries a radiation sensing arrangement whose purpose is explained below.

In use, after an image of the internal part of the patient has been obtained, the patient is moved to a treatment position, e.g. an operating table, to which the frame is secured in known fixed positional relationship. A surgical tool to be used in the treatment which carries a radiation emitting arrangement which produces signals which can be detected by the sensing arrangement on the frame is then positioned adjacent the patient's body. The signals picked up by the sensing arrangement from the emitting arrangement are passed to electronic apparatus which utilises the signals to determine the position and orientation of the tool with respect to the operating table.

The position and orientation of the part of the patient to be treated with respect to the operating table is determined by indicating to the electronic apparatus the position of the set of markers attached to the patient. Output signals of the electronic apparatus representative of the positions and orientation of the set of markers and hence the patient's body and of the position and orientation of the surgical tool are utilised to place on a display of the previously obtained image of the patient's body a representation of the tool at a position and orientation with respect to the image corresponding to the position and orientation of the tool with respect to the actual patient's body on the operating table.

One problem which arises with such a system is the requirement to attach a set of markers to the patient's body. If the treatment is carried out over a period of time, it is necessary for the markers to remain on the patient's body throughout the period of treatment so that a correct registration of the image of the patient and the representation of the surgical tool can be obtained each time the patient is brought to the operating table.

It is an object of the present invention to provide an imaging system wherein this problem is overcome.

According to the present invention there is provided an imaging system comprising: imaging apparatus for obtaining an image of an internal part of an object placed in an examination region of the imaging apparatus; a reference frame which carries a radiation sensing arrangement and is fixed with respect to a treatment position; a tool which is required to be accurately positioned with respect to the object when the object is in the treatment position; a radiation emitting arrangement associated with the tool which emits radiation for detection by the sensing arrangement to produce signals indicative of the position of the tool with respect to the reference frame; and display means for displaying said image of the object and utilising said signals produced by said sensing arrangement to provide a representation of said tool in said display at a position and orientation with respect to said image of the object corresponding to the position and orientation of the tool with respect to the actual object; characterised in that said reference frame and hence said treatment position is fixed in position with respect to said examination region.

A system according to the invention preferably further includes: transport means; support means on which the object is mounted during imaging and treatment; and guide means along which the support means travels when moving between the examination region and the treatment position.

Such a system preferably further includes means for monitoring the position of the support means relative to the rail means to determine variations in the position of the support means when in the transport position.

The system suitably further includes means for monitoring the position of the object relative to the support means.

One imaging system in accordance with the invention for use in carrying out medical stereotactic surgical procedures will now be described, by way of example, with reference to the accompanying drawings in which:

FIG. 1 is schematic diagram of a magnetic resonance imaging apparatus used in the system;

FIG. 2 is a diagrammatic representation of a treatment position of the system and a transport means of the system for transporting a patient between the treatment position and the imaging apparatus; and FIG. 3 depicts a scale forming part of a position monitoring means of the system.

Referring to FIG. 1, the magnetic resonance imaging apparatus of the system includes a tubular electromagnet structure 1 which produces a strong uniform static main axial magnetic field in a cylindrical examination region 3 in which the part of a patient's body to be imaged and subsequently treated is placed in use of the apparatus.

The strength of the field in the region 3, and hence in the body being imaged, is controlled by a main magnetic field control means 7 which controls the supply of energising current to the electromagnet energising coil (not shown).

The apparatus further includes a gradient coil arrangement 9 whereby a gradient magnetic field may be imposed on the static magnetic field in the region 3 in a direction parallel to the static field with a gradient in any one or more of three orthogonal directions. The coil arrangement 9 is energised by a gradient field control means 11 under control of a computer 5.

The apparatus further includes an r.f. coil system 13 energised by an r.f. transmitter 15 under control of the computer 5 to apply an r.f. field to the body being imaged.

An r.f. receiver coil arrangement 17 is arranged to detect r.f. signals resulting from magnetic resonance excited in the body being imaged. The detected signals are passed via a receiver 19 to an imager 21 which under control of the computer 5 processes the signals to produce signals representing an image of the body. These signals are, in turn, passed to a display device 23 to provide a visual display of the image.

In operation of the apparatus the strong magnetic field provided by the electromagnet 1 defines an equilibrium axis of magnetic alignment in the body being imaged.

To obtain an image of a selected region, e.g. a cross-sectional slice, of the patient's body, an r.f. field pulse is first applied to the body by means of the coil system 13 to excite magnetic resonance in the selected region. To this end the coil system 13 produces a field in a direction orthogonal to the static field direction so as to tip the spins of nuclei in the selected region from the direction of the static field into a plane orthogonal to the static field direction. To restrict excitation to the selected region the r.f. field pulse is applied in conjunction with magnetic field gradients imposed by the coil arrangement 9, the frequency of the r.f. field being chosen in conjunction with the magnitudes and directions of the imposed gradients so that the Larmor frequency of chosen protons in the body, e.g. hydrogen protons, is equal to the r.f. field frequency only in the selected region.

The r.f. signals resulting from excitation are then spatially encoded by application of one or more further gradient magnetic fields in known manner, detected by the r.f. coil arrangement 17, and processed to produce an image.

Normally a number of excitation and signal detection sequences are required to produce sufficient data to produce a satisfactory image.

It will be appreciated that the foregoing description of operation merely illustrates one basic mode of operation, and that the apparatus can be used to obtain an image of a subject of interest in many different known modes, each involving application of different sequences of r.f. pulses and magnetic field gradients.

Referring now to FIG. 2, after obtaining an image or set of images of the part of the patient to be treated using the imaging apparatus, as described above, the patient is moved from the examination region 3 to a treatment position 25. To facilitate this the system incorporates a transport means 27 comprising a horizontal support means 29 on which the patient lies, and a pair of rails 31 on which the support means 29 runs so that the support means 29, and hence the patient, can be rapidly moved between the examination region 3 and the treatment position 25.

At the treatment position 25 the rails 31 are supported on a table 33 which is rigidly secured in position with respect to the imaging apparatus, i.e. by virtue of the table 33 and imaging apparatus both being securely mounted on the floor (not shown) of the room housing the system. Consequently, when moved to the treatment position the patient's body is located at an accurately known distance from the position in which it was during imaging, and in the same orientation with respect to the imaging apparatus as it was during imaging.

The imaging system further includes means whereby an indication of the position and orientation of a surgical tool with respect to a patients body is given in the display of the image obtained by the imaging apparatus. To this end the system includes a rectangular frame 35 which is supported from the electromagnet structure 1 of the imaging apparatus so as to be in a fixed position relative to the region 3. At each corner of the frame 3 there is mounted a radiation detector 37. The radiation detectors 37 are suitably responsive to ultrasonic pressure waves, but may be responsive to other kinds of radiation e.g. short wavelength radio waves or infrared waves. In addition, each surgical tool it is desired to use is arranged to fit into a tool guide 39 which carries an emitter arrangement (not shown) for emitting the radiation to which the detectors 37 are responsive. The tool guide 39 suitably comprises a tubular portion 39A adapted to receive the body of any selected surgical tool (not shown) and a handle portion 39B by means of which a surgeon may hold the guide 39 whilst finding the best position in which to use the tool.

From measurements of the times taken for radiation to travel from the emitter arrangement on the tool guide 39 to the different detectors 37, the location of the toolguide 39, and hence a tool fitted into the guide 39, with respect to the frame 35 can be accurately determined. By making measurements for at least two emitters at different locations on the tool guide 39, the orientation of the tool guide 39 and tool can also be determined.

Whilst only three detectors 37 are necessarily required on frame 35, the use of more than three detectors 37 allows improved accuracy by averaging. Similarly more than two emitters may be provided on the tool guide 39.

The tool guide emitters, instead of being mounted directly on the tool guide 39, may be mounted on a so-called wand (not shown) which is inserted in the tool guide 39, to enable the surgeon to position the tool guide 39 in a desired position using the display provided by the system. The wand is then removed from the tool guide 39 and the required tool inserted in its place.

It will be understood that instead of using a tool guide, individual tools may be provided with their own emitting arrangements:

The signals required to add a representation of the tool to the display of the image obtained by the imaging apparatus are fed to the imager 21 by a processor 41 in response to the output signals of the detectors 37 and timing signals from a transmitter 43 which provides energising pulses to the emitting arrangement of the tool guide 39, under control of the computer 5. It will be understood that the provision of such signals to the imager 21 is made possible by the fact that the frame 35 and hence the detectors 37 are rigidly fixed at a known position with respect to the imaging apparatus and hence the examination region 3, and the movement undergone by the patient's body during transport from the examination region 3 of the imaging apparatus to the treatment position 25 is accurately known.

It will be understood in this connection that in the embodiment described by way of example, since the table 33 is fixed with respect to the imaging apparatus, the frame 35 can alternatively be mounted on the table 33. Furthermore, the frame 35 is not necessarily positioned in a plane parallel to the direction of motion of the support means 29, as shown in FIG. 2, but may be positioned, for example, in a plane transverse to that direction.

In order to monitor any deviations in the movement of the patient support 29 from the intended movement, i.e. along a straight line of known length, the underside of the support 29 carries a scale which is viewed by a detector arrangement (not shown) mounted on the table 33. Suitably the scale is in the form of a set of markings, as illustrated in FIG. 3, comprising a pair of parallel lines 43 extending in the direction of travel of the support 29 on the rails 31, at a known spacing L, and a series of lines 45 extending between the lines 43, at right angles thereto, at equal spacings from one another. The detector arrangement suitably comprises light emitting diodes illuminating the scale and charge coupled devices viewing the illuminated scale through appropriate optical devices. The parameters detected, as illustrated in FIG. 3, are: $\propto$, the yaw angle, $\Delta$, and $\Sigma$, which together give a measure of lateral shift and roll, if present; and $\delta$, which gives a measure of the error in the direction of travel of the support 29. The angle of roll $\beta$ undergone is given by the expression:

$$\beta = \cos^{-1}\left\{ \frac{L - (\Sigma + \Delta)}{L} \right\}$$

Similarly, tilt can be obtained by measuring the distances between adjacent pairs of the transverse lines 45.

Monitoring means (not shown) may also be provided, if desired, for monitoring movement of the patient relative to the support 29. Such monitoring means suitably comprises a belt wrapped around the patient with light emitting sources mounted on it, and solid state optical scanning devices, such as charge coupled devices with appropriate optical devices, mounted one on each side of the support 29. Further monitoring means in the form of sensors located under the imaging apparatus to provide a measurement of the position of the patient when in the examination region 3 may be provided.

The various position measurements made by the above described monitoring means may be used to adjust the patient image and tool representations positions in the display, so that the relative positions of image and representations correctly indicate the actual relative positions of the tool and patient's body. Alternatively, the scanning angles and axes used in the imaging apparatus may be altered to effect the required correction in the display.

It will be understood that preferably all positional data is referenced to, and corrected for, deviations from positions established at the commencement of a surgical procedure.

It is pointed out that whilst the present invention renders the attachment of markers to a patient's body unnecessary, it may be desirable, in some procedures, to attach such markers to provide an additional check on relative positions of image and tool. The positions of the markers can of course, be indicated, in known manner, to the display means by touching them with a wand carrying, emitters as described above.

It is pointed out that whilst in the particular imaging system described above, by way of example, the imaging apparatus is a magnetic resonance imaging apparatus, other types of imaging apparatus may be used in other systems according to the invention, for example, x-ray tomography imaging apparatus, in particular, a computed tomography (CT) imaging apparatus. In such a system the reference frame is suitably mounted on the gantry of the tomography apparatus which supports the rotatable member on which the x-ray source of the apparatus is mounted. It is further pointed out that use of an imaging system according to the invention is not restricted to surgical procedures. The invention may find application wherever it is desired to position a tool adjacent an object using an image of an interior part of the object.

What is claimed is:

1. An imaging system comprising:
    an imaging apparatus for obtaining an image of an internal part of an object placed in an examination region of the imaging apparatus;
    an object support adapted to support the object and movable between first and second positions, whereby the object is positioned in the examination region when the support is in the first position and in a treatment position when the object support is in the second position;
    a reference frame which carries a radiation sensing arrangement and which is fixed with respect to the second position;
    a tool which is required to be accurately positioned with respect to an internal region of the object when the object is in the treatment position;
    a radiation emitting arrangement associated with the tool which emits radiation for detection by the sensing arrangement to produce signals indicative of the position of the tool with respect to the reference frame; and
    display means for displaying said image of the object and utilizing said signals produced by said sensing arrangement to provide a representation of said tool in said display at a position and orientation with respect to said image of the object corresponding to the position and orientation of the tool with respect to the actual object, said reference frame and said second position being fixed in position with respect to said examination region.

2. A system according to claim 1 wherein said imaging apparatus is a magnetic resonance imaging apparatus.

3. A system according to claim 2 wherein said reference frame is mounted on a magnet arrangement which produces a magnetic field for defining an equilibrium axis of magnetic alignment in an object being imaged.

4. A system according to claim 1 wherein said imaging apparatus is a computed tomography x-ray apparatus.

5. A system according to claim 1 wherein said radiation sensing arrangement is responsive to ultrasonic radiation.

6. A system according to claim 1 further including
    a guide along which the object support travels when moving between the first and second positions.

7. A system according to claim 6 further including means for monitoring the position of the support relative to the guide to determine variations in the position of the support when in the second position.

8. A system according to claim 7 wherein said monitoring means includes a light sensing device.

9. A system according to claim 6 further including means for monitoring the position of the object relative to the support means.

10. A system according to claim 9 wherein said means for monitoring the position of the object includes a light sensing device.

11. An imaging system comprising:
    an imaging apparatus for obtaining an image of an internal part of an object placed in an examination region of the imaging apparatus;
    an object support on which the object is mounted during imaging and treatment and which is movable between the examination region and a treatment position;
    a guide along which the object support travels when moving between the examination region and the treatment position;
    a reference frame which carries a radiation sensing arrangement and which is fixed with respect to the treatment position;
    a tool which is required to be accurately positioned with respect to the object when the object support and hence the object is in the treatment position;
    a radiation emitting arrangement associated with the tool which emits radiation for detection by the sensing arrangement to produce signals indicative of the position of the tool with respect to the reference frame;
    optical means for monitoring the position of the object support relative to the guide to determine variations in the position of the support when the support is in the treatment position, said optical monitoring means comprising a set of markings fixed relative to one of said object support and said guide and a device for viewing the markings secured to the other of said object support and said guide; and
    display means for displaying said image of the object and utilizing said signals produced by said sensing arrangement to provide a representation of said tool in said display at a position and orientation with respect to said image of the object corresponding to the position and orientation of the tool with respect to the actual object, said reference frame and said treatment position being fixed in position with respect to said examination region.

12. A system according to claim 11 wherein said guide constrains the object support to travel nominally along a straight line and said set of markings comprises parallel spaced lines parallel to said straight line and parallel spaced lines orthogonal to said straight line.

13. A method of determining the position of a tool with respect to an internal part of an object placed in the examination region of an imaging apparatus, the method comprising the steps of:

placing an object on an object support;

moving the object support to an examination position whereby the object is within the examination region;

obtaining an image of the object;

moving the object support to a treatment position, the treatment position being fixed in position with respect to the examination region;

positioning a tool with respect to an interior region of the object, said tool comprising a radiation emitting arrangement;

detecting the emitted radiation using a radiation sensing arrangement carried on a reference frame fixed in relation to the examination region;

displaying the image of the object, the displayed image including a representation of the tool at a position and orientation corresponding to the position and orientation of the tool with respect to the actual object.

14. A method according to claim 13 wherein the step of obtaining an image includes the step of utilizing a magnetic resonance imaging apparatus.

15. A method according to claim 13 wherein the step of detecting the emitted radiation includes the step of detecting ultrasonic radiation.

16. A method according to claim 13 wherein the step of moving the object support to the examination position includes moving the object support along a guide.

17. A method according to claim 16 further including the step of monitoring the position of the object support relative to the guide to determine variations in the position of the support when the support is in the treatment position.

18. A method according to claim 16 further comprising the step of monitoring the position of the object relative to the object support.

19. A method of determining the position of a tool with respect to an internal part of an object placed in the examination region of an imaging apparatus, the object being mounted on an object support, the object support traveling along a guide when moving between the examination region and a treatment position, the method comprising the steps of:

obtaining an image of the object;

moving the object to the treatment position, the treatment position being fixed in position with respect to the examination region;

positioning a tool with respect to the object, said tool comprising a radiation emitting arrangement;

detecting the emitted radiation using a radiation sensing arrangement carried on a reference frame fixed in relation to the examination region;

utilizing a set of markings fixed relative to one of said object support and said guide and a device for viewing the marking secured to the other of said object support and said guide to monitor the position of the object support relative to the guide to determine variations in the position of the support when in the treatment position;

displaying the image of the object, the displayed image including a representation of the tool at a position and orientation corresponding to the position and orientation of the tool with respect to the actual object.

20. A method comprising:

placing a patient on a patient support movable between a first position and a second position such that the patient is positioned in the examination region of a medical imaging apparatus when the patient support is in the first position and in a treatment position when the patient support is in the second position, the second position having a substantially known relationship with respect to the examination region;

moving the patient support to the first position;

obtaining an image of the patient;

moving the patient support to the second position;

when the patient support is in the second position, determining a deviation between the actual and expected positions of the patient support;

positioning a surgical tool with respect to the patient;

determining a position of the surgical tool;

displaying the image of the patient, the displayed image including a representation of the tool at a position on the image corresponding to the position of the tool with respect to the patient, the relative position of the representation and the image being adjusted to account for the determined deviation.

21. The method of claim 20 wherein the step of determining a deviation includes determining the yaw angle of the patient support.

22. The method of claim 20 wherein the step of determining a deviation includes determining the lateral shift and roll of the patient support.

23. The method of claim 20 wherein the step of determining a deviation includes determining the tilt of the patient support.

24. The method of claim 20 wherein the step of determining a deviation includes determining a position error in a direction of travel of the patient support.

25. The method of claim 20 wherein the patient support has a longitudinal axis and the step of moving the patient support to the second position includes moving the patient support along its longitudinal axis.

26. The method of claim 20 wherein the step of determining a position of the surgical tool includes utilizing a radiation detecting arrangement having a known position with respect to the examination region to detect radiation indicative of the position of the tool.

27. The method of claim 26 wherein the step of determining the position of the surgical tool includes using radiation emitters located on the surgical tool to emit radiation detectable by the radiation detecting arrangement.

28. The method of claim 20 wherein the tool is a tool guide.

* * * * *